US010405964B2

(12) United States Patent
Hannes et al.

(10) Patent No.: US 10,405,964 B2
(45) Date of Patent: Sep. 10, 2019

(54) IMPLANT COMPRISING A NON-WOVEN FABRIC

(75) Inventors: Ralf Hannes, Dortmund (DE); Hermann Monstadt, Bochum (DE)

(73) Assignee: Phenox GmbH, Bochum (DE)

( * ) Notice: Subject to any disclaimer, the term of this patent is extended or adjusted under 35 U.S.C. 154(b) by 0 days.

(21) Appl. No.: 14/000,576

(22) PCT Filed: Feb. 27, 2012

(86) PCT No.: PCT/EP2012/000841
§ 371 (c)(1),
(2), (4) Date: Oct. 28, 2013

(87) PCT Pub. No.: WO2012/113581
PCT Pub. Date: Aug. 30, 2012

(65) Prior Publication Data
US 2014/0058498 A1 Feb. 27, 2014

(30) Foreign Application Priority Data

Feb. 25, 2011 (DE) .................. 10 2011 012 501

(51) Int. Cl.
| | |
|---|---|
| *A61F 2/07* | (2013.01) |
| *A61F 2/86* | (2013.01) |
| *A61F 2/90* | (2013.01) |
| *A61L 31/10* | (2006.01) |
| *A61L 31/14* | (2006.01) |
| *A61L 31/16* | (2006.01) |
| *D01D 5/00* | (2006.01) |
| *D01F 6/70* | (2006.01) |
| *A61F 2/82* | (2013.01) |
| *A61F 2/95* | (2013.01) |

(52) U.S. Cl.
CPC .................. *A61F 2/07* (2013.01); *A61F 2/86* (2013.01); *A61F 2/90* (2013.01); *A61L 31/10* (2013.01); *A61L 31/146* (2013.01); *A61L 31/16* (2013.01); *D01D 5/0084* (2013.01); *D01F 6/70* (2013.01); *A61F 2002/075* (2013.01); *A61F 2002/823* (2013.01); *A61F 2002/9505* (2013.01); *A61L 2300/41* (2013.01); *A61L 2300/416* (2013.01); *A61L 2400/16* (2013.01)

(58) Field of Classification Search
CPC .................. A61F 2/07; A61F 2002/072; A61F 2210/0076; D01D 5/0084; A61L 31/146
USPC .................................. 623/1.13, 1.49
See application file for complete search history.

(56) References Cited

U.S. PATENT DOCUMENTS

| | | | |
|---|---|---|---|
| 4,550,447 A | * | 11/1985 | Seiler et al. .................. 623/1.32 |
| 8,945,161 B2 | | 2/2015 | Miloslavski et al. |
| 9,034,026 B2 | | 5/2015 | Hannes et al. |
| 9,107,670 B2 | | 8/2015 | Hannes et al. |
| 2009/0088828 A1 | * | 4/2009 | Shalev et al. .................. 623/1.2 |
| 2009/0198269 A1 | | 8/2009 | Hannes et al. |
| 2009/0306702 A1 | | 12/2009 | Miloslavski et al. |
| 2010/0152834 A1 | | 6/2010 | Hannes et al. |
| 2011/0060359 A1 | | 3/2011 | Hannes et al. |
| 2011/0184451 A1 | | 7/2011 | Sahl |
| 2011/0238148 A1 | | 9/2011 | Monstadt et al. |
| 2013/0138198 A1 | | 5/2013 | Aporta et al. |
| 2013/0211492 A1 | | 8/2013 | Schneider et al. |
| 2013/0296916 A1 | | 11/2013 | Monstadt et al. |
| 2014/0058420 A1 | | 2/2014 | Hannes et al. |
| 2014/0343595 A1 | | 11/2014 | Monstadt et al. |

FOREIGN PATENT DOCUMENTS

WO WO2006/123340 A2 11/2006

OTHER PUBLICATIONS

Collins English Dictionary; Definition of "Sponge".*
Collins English Dictionary; Definiton of "Elastomer".*

* cited by examiner

*Primary Examiner* — Brian A Dukert
(74) *Attorney, Agent, or Firm* — Brooks Kushman P.C.

(57) ABSTRACT

The invention relates to a membrane implant for the treatment of vascular malformations, said implant being implantable by endovascular methods into the vessel to be treated, wherein the membrane implant consists of an expandable stent (4) and a membrane (3, 5, 11, 2) connected with the stent (4), with said membrane (3, 5, 11, 4) covering the meshes of the stent (4) at least in a central region, wherein said membrane (2, 3, 5, 11) is provided in the form of a non-woven fabric comprising plastic fibrils, and the membrane (2, 3, 5, 11) forms an integral bond with the stent (4) and, at least partially, is of porous design.

16 Claims, 2 Drawing Sheets

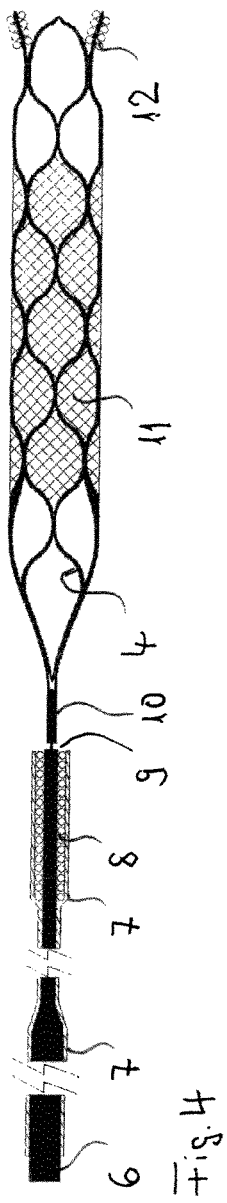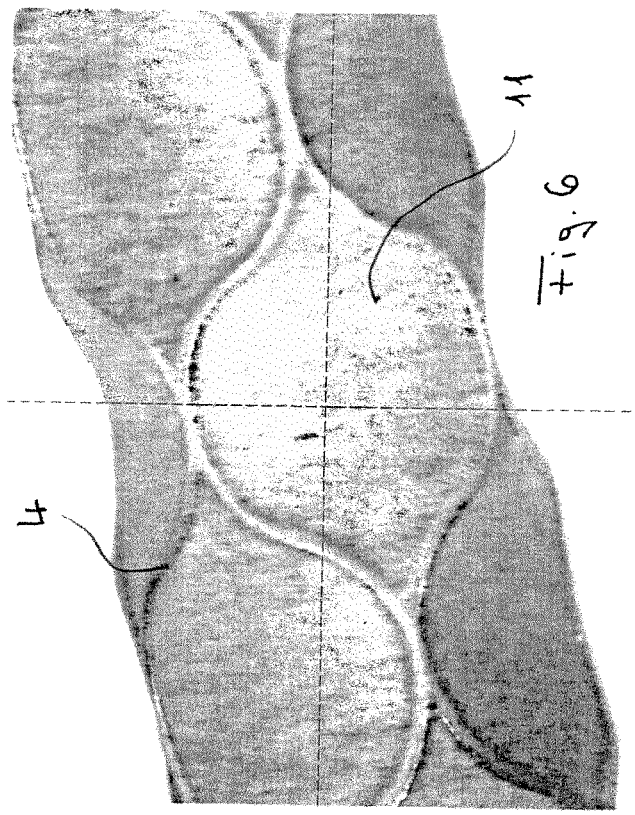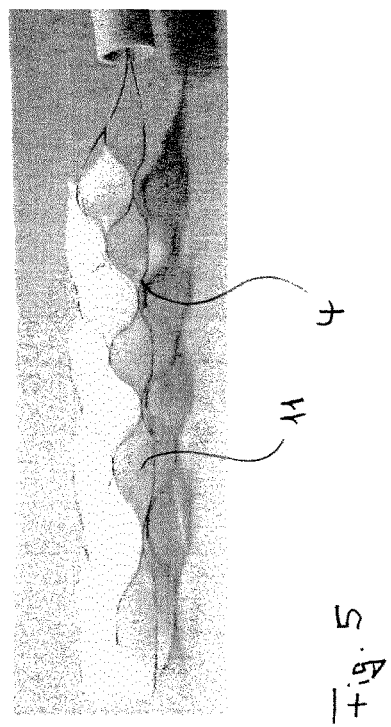

IMPLANT COMPRISING A NON-WOVEN FABRIC

BACKGROUND OF THE INVENTION

Field of the Invention

The invention relates to a membrane implant for the treatment of vascular malformations, said implant consisting of an expandable stent and a membrane connected to said stent, wherein the membrane covers meshes of the stent at least in a central area. The membrane implant is intended for implantation by endovascular method into a patient's vascular system to be treated.

Related Art

For the treatment of vascular malformations, in particular of the arteries, which are usually confined to a very small region a multitude of instruments have been developed which either exclusively or preferably exert a local effect of a mechanical, thermal, chemical, electrical or pharmaceutical nature. These treatment methods are mainly based on endovascular techniques by means of which the treatment instrument is guided via a catheter to the placement site and applied there.

A commonly used form of treatment, especially in connection with sclerotic constrictions of vessels but also to bridge aneurysms or other arteriovenous malformations is the placement of stents used to expand the constricted location or bridge the malformation. A plurality of stent types have been developed and are in use.

Basically, there are two stent types. These are on the one hand balloon-expandable stents which in most cases are made of steel suitable for medical purposes and transported by means of a balloon catheter to the placement site where they are expanded hydraulically. On the other hand, stents are used that are made of self-expanding material, for example nitinol, and advanced in contracted form by means of a catheter to the placement site where they are released assuming in liberated state their expanded shape as envisaged. Both stent types may be combined with drugs having in particular anti-inflammatory or antistenotic effects.

A stent variant which in particular serves to bridge vascular deformities is a stent provided with a membrane, wherein the stent impedes the ingress of blood from the vessel into the deformity or even prevents it. In the event of an aneurysm or shunt this as a rule leads to the formation of a clot in that location causing the aneurysm or shunt to be occluded. Such a membrane implant has, for example, been described in WO 2010/006777 A1.

As already mentioned hereinbefore, stents and other implants for the treatment of arteriovenous malformations and stenoses are often combined with medications to assist in this way the purely mechanical effect of the implant as a result of the pharmacological properties of these substances. Especially coatings provided with proliferation-inhibiting substances such as paclitaxel and rapamycin have proven their worth. Numerous other active ingredients have been described for use in conjunction with stents in vessels, in particular to prevent the occurrence of restenosis. Restenoses most frequently occur within the first few weeks after the implantation of stents and are often due to damage caused to the vessels during the stent implanting process.

The coating of stents and other implants with active pharmaceutical substances is highly problematic, especially as regards the fixation of the active agent on the stent surface and their uniform dispensation throughout the relevant period of time. Of importance is that a low and constant effective concentration is available over the desired time span. Since the active substances are highly effective medical agents dispensation peaks must be avoided and dispensation itself should be limited to the desired time period. Taking the customary stent designs and membranes this requirement is difficult to achieve.

Membrane coated implants must not necessarily be coated with drugs. To occlude a malformation it is usually sufficient to isolate the malformation to be treated from the blood circulation system. Various plastic membranes were developed for this purpose which, for example, are made of polytetrafluoroethylene, polyester, polyamide or polyolefin. However, membranes of this kind have a disadvantage in that they are not readily attached to the stent that carries them but are retained virtually mechanically at the vessel wall by the expanding stent. A connection to the stent structure itself would be desirable. Another desirable feature would be a structure that enables the pressure exerted by the stent on the vessel wall when expanding to be appropriately distributed so that a risk of injury could be minimized in this way.

Therefore, the objective of the present invention is to provide a membrane implant that enables an integral connection with the stent to be realized, wherein the membrane is suitable to function both as a "cushion" located between the vessel wall and the stent and as a barrier erected to occlude a vessel malformation. Moreover, it would also be desirable to provide a suitably designed membrane capable of accommodating drugs or medical substances and dispense them uniformly over a desired period of time to the neighboring vessel wall.

For this purpose, the membrane implant is provided with a membrane made of a non-woven fabric and comprising plastic fibrils, wherein the membrane is integrally connected with the stent and, at least partially, of porous design. Due to its porous structure the membrane is capable of accommodating drugs and dispensing these medical substances under physiological conditions to the surrounding vessel wall.

The membrane of the membrane implant according to the invention is a non-woven fabric composed of plastic fibers or fibrils and directly attached to the stent structure. Typically, the stent structure itself can be used to deposit the fibrils or fibers of the non-woven fabric onto the stent, for example by immersion or spray coating using a suitable solution or emulsion. For this purpose, the fibers may be deposited in an aligned or non-aligned manner. The type of deposition as well as the fiber size and layer thickness have an influence on the porosity.

The membrane on the stent is preferably made by electrospinning of a non-woven fabric. By applying an electric current the fibrils or fibers of the non-woven fabric are separated from a polymer solution and deposited on a substrate. Said deposition causes the fibrils to agglutinate into a non-woven fabric. As a rule, the fibrils have a diameter ranging between 100 and 1000 nm. Membrane implants produced by electrospinning comprise a very thin and uniformly built membrane which readily forms a bond with the stent framework and in this manner is suited to embrace the stent framework. The membrane is tenacious, withstands mechanical stresses, and can be easily pierced mechanically without an opening so created giving rise to cracks propagating from it. Thickness and length of the fibrils as well as the degree of porosity can be controlled by selecting process parameters as appropriate.

As membrane material any biocompatible material approved for such applications may be employed, for example polyester, polyamide, polyurethane, polytetrafluoroethylene or similar materials. Especially preferred is polyurethane, resp. a copolymer known as polycarbonate urethane. In the context of producing the membrane and with respect to materials suitable for this purpose attention is drawn to publications WO 2008/049386, DE 28 06 030 and the literature referred to therein.

The membrane employed according to the invention is at least partially porous. Partially porous in this context means the membrane side (outside) facing the vessel wall has pores whereas the membrane side (inside) facing the vessel is designed so as to be substantially liquid-tight.

The membrane as proposed by the present invention as a rule has pores 1 to 100 μm in size, particularly in the range of between 10 and 50 μm. The diameter of the fibrils ranges between 0.5 and 100 μm and their length is between 10 μm and 1 mm.

Depending on the size of the vessel a pore size of about 20 to 50 μm has turned out to be especially favorable with regard to the ingrowth of endothelial cells.

The membrane may be composed of a single layer, i.e. it may be applied to the stent structure in a single work cycle. As a rule, it will be designed so as to comprise several, in particular two or three layers. The inner layer of the membrane may be the above mentioned substantially liquid-tight layer. On the other hand, the outer layer of the membrane facing the vessel wall is of porous or spongy design so that it is also capable of accommodating an active agent in a suitable carrier substance and dispense said agent to the vessel wall through the pores. The active agent may be introduced into the pores by immersion or spraying. Providing a middle layer of a dense fiber compound will result in the membrane strength being increased.

A multi-layer embodiment may as well be provided, wherein the individual layers are produced by different methods, for example an inner layer by electrospinning, a second layer by spray coating and a third layer by electrospinning. In this way, the advantages the different methods offer can be made use of, especially with regard to achieving optimum results in terms of porosity, strength or impermeability.

The active agent may also be incorporated into the layer matrix of a one- or multi-layer system, i.e. also into an inner layer. The agent will then be released by diffusion through the matrix or as a result of a degradation or erosion of the polymer.

Also radiopaque substances can be incorporated into the layer system, said substances being helpful in the placement or control of the implant. Such radiopaque substances may, for example, be salts of heavy metal such as barium sulfate or iodine compounds as they are commonly used as contrast medium for radiographic examination purposes.

In the event the inventive membrane implant is intended to influence the blood flow, for example to bridge an aneurysm, a thin membrane will be sufficient in most cases, with the inside of said membrane having substantially liquid-tight properties. In this case as well the outside is designed so as to be porous to assist the ingrowth of endothelial cells.

From a manufacturing point of view it is usually advantageous for multi-layer membranes, however, to arrange for the inner as well as outer layers to be identical in terms of impermeability, porosity or strength. This, in particular, enables the stent structure to be embedded or wrapped up in the membrane and in this way create a composite combining the stent with the membrane. The webs of the stent are surrounded on all sides by membrane material in this way.

In any case, the inventive membrane will definitely cover the central region of the stent, respectively the stent structure. Nevertheless, it is considered expedient for it to encompass and cover the entire stent so that via the membrane the entire length of the stent is in contact with the vessel wall.

The membrane of the membrane implant is produced, in particular, by spray coating using a suitable plastic solution, wherein said coating can be built up in several work cycles. The stent in that case may serve as primary carrier or matrix, i.e. the coating is directly sprayed onto the honeycombs or meshes of the stent until these have been sealed by the membrane thus formed. As an alternative, the stent may also be mounted on a mandrel, then spray coated from the outside and subsequently removed from the mandrel. For spray coating purposes nozzles are to be used that in particular are suited for the production of fibers.

Also possible is the adoption of a so-called electrospinning process for this purpose as it has frequently been described in technical literature. In this case as well individual fibers are deposited onto the stent surface, with said fibers, depending on the deposition density, resulting in the formation of a more or less porous mesh.

When applying the coating it must by all means be ensured that the fibers are formed into a sufficiently firm and dense bond with each other as well as with the stent framework. Usually, the fibers have an adhesive tendency as soon as they are deposited. However, this may also be achieved by using an adhesive material or by subsequently carrying out a mechanical, thermal or other kind of treatment aimed at gluing and/or welding the individual fibers. For example, ultrasound may be successfully applied here, as it may also be used to "break up" the fiber structure with a view to increasing the porosity. The electrospinning process enables the fiber thickness, porosity, and the degree of adhesion to be controlled via the speed.

With respect to optimize/improve the strength of the bond between non-woven fabric and stent structure an adhesion-promoting layer may be applied at least on the outside of the stent framework. For this purpose, immersion and spraying methods with polymers can be employed or deposition processes such as the chemical vapor deposition (CVD) process using parylenes.

The membrane on the stent framework usually has a layer thickness of 10 to 400 μm, in particular 10 to 100 μm and especially preferred 10 to 40 μm. The thickness of the layers depends on the intended use. The layer thickness (and porosity) of membranes intended to accommodate formulations of drugs is usually greater than in membranes that exclusively have to perform a barrier function.

For the design of the membrane it may be expedient to provide several layers, the fibers of each of these layers being differently aligned. This may not only have an influence on the porosity but may also have an effect on flexibility as well as frictional properties. For instance, by purposefully aligning the fibers on the outer membrane surface the membrane's gliding properties in the catheter can be positively influenced, in particular when providing a parallel alignment in the longitudinal direction of the implant. This enables the implant to be easier pushed forward in the catheter during placement.

It is known that the use of polycarbonate urethane results in the membrane being highly biocompatible. Moreover, due to porosity the ingrowth of endothelial cells is promoted so that the implant can be integrated into the vessel wall. Same as many other plastic substances polycarbonate urethane degrades in the body over time causing the membrane to have dissolved after some time.

The material and design of the stent of the inventive membrane implant can be selected so that the stent may perform various tasks as desired. Same as the membrane, the stent may be self-dissolving, for example by using pure iron, magnesium, magnesium alloys or cobalt-chrome alloys.

As stent framework any customary stent may be employed that is suitable for implantation into a vessel. Preferred however are stents that have a relatively low framework density, which means they are for the main part of open design, because in that case the stent exclusively serves to attach the membrane to the vessel surface. A supporting effect is not always required. In case a supporting effect is to be achieved, the stent has to be designed to meet this requirement. Especially for membrane stabilizing purposes an increased framework density (small meshes) is advantageous.

As proposed by the present invention also self-expanding stents may be used, as they are manufactured from shape-memory materials. Known are stents made of nitinol or a ternary nickel-titanium alloy, said stents can be transported in contracted shape restrained inside a catheter, having been released from the catheter assume their impressed expanded shape, and attach via their membrane to the vessel wall. Such stents are particularly suited for membrane implants serving to influence the flow, for example to occlude vessel malformations such as aneurysms.

The stents may be cut in a customary manner from a tubular body, however so-called braided stents made from a suitable wire material may be employed as well. Especially the latter can be applied as "neurostents" for the purpose of bridging aneurysms or other vascular malformations in the brain.

Using stents made of wire or stents having a low framework density in connection with flexible membranes of non-woven fabric enables the production of highly flexible and thin membrane implants which may also be introduced without difficulty into vessels of small lumen. Such flexible stents for small-lumen vessels are especially made use of in neuroradiology.

Also proposed by the invention is that the membrane implant may consist of a combination of two outer stents with a membrane of non-woven fabric arranged in between. Also conceivable is that the stent framework is provided with a membrane of non-woven fabric only on its outside or only on its inside. Another alternative provides for the inventive membrane implant to be manufactured in such a manner that a stent located inside is surrounded by the membrane from all sides resulting in preventing both the vessel wall and the blood from coming into contact with the stent framework. According to the invention, preference is given to a stent that is covered on both sides by the non-woven fabric. This means the webs or struts of the stent are embedded in and surrounded by the non-woven fabric material.

In the event the membrane implant according to the invention is to accommodate a drug such medical substances are preferably applied to the outer membrane layer facing the vessel. To this effect, this layer is in particular designed to have a sponge-like texture. Initially, the expansion pressure produced thus causes the drug in this case to be first "pressed out" in greater volume but subsequently it is uniformly dispensed to the vessel wall over a certain period of time. For local application purposes and depending on the type of disease there is a variety of suitable very different drugs. For prophylaxis and therapy of vasoconstrictions as well as other mainly space-occupying processes cytostatically active substances are used as they are, for example, applied to stents or balloon catheters in the therapy of tumors or for the prophylaxis of restenoses.

For the treatment of, for example, inflammatory, lipid-rich or infectious vessel wall alterations having minor or no stenotic effects cytostatic drugs due to their anti-inflammatory properties, immunosuppressants, steroidal and non-steroidal antiphlogistics, statins, antioxidants, coagulation inhibitors or mixtures of individual active substances can be used. A plurality of such substances have been described in textbooks of pharmacology and numerous patents, such as, for example, in publication US 2008/0118544 or DE 10 2007 036 685. Preferred agents are paclitaxel, docetaxel, protaxel and other taxanes, methotrexate, 2-deoxyglucose, thalidomide, triamcinolone, betamethasone, dexamethasone and their derivatives, genistein, sirolimus, everolimus and other mTOR inhibitors, artorvastatin, cerivastatin, fluvastatin, lovastatin, pitavastatin, pravastatin, rosuvastatin, simvastatin, doxycycline, minucycline, probucol, tocopherol, ascorbic acid, arsenic trioxide, and other arsenic salts and compounds, bismuth salts and compounds. To the extent applicable the relevant active substances can also be used in the form of salts or complex compounds or having covalent bonds, for example in the form of prodrugs or their effective derivatives. To the extent required, mixtures of certain active substances may be used, wherein each active substance being dosed according to its potency.

The inventive membrane implant is transported to its placement site by means of a customary catheter. If the stent is of balloon expanding type it is crimped together with the membrane onto a balloon in the usual way. In the event of a self-expanding stent the membrane-carrying stent can be placed via catheter and guidewire. The techniques adopted for this purpose are generally known to those skilled in the art.

The inventive membrane implants can be manufactured by customary immersion and spray-coating methods, wherein a number of work steps are involved to provide the stent framework with the membrane. Preferred, however, is an electrospinning process that, to produce the membrane, makes use of a plastic solution in an organic solvent, for example polycarbonate urethane in chloroform. This process provides for the non-woven fabric later located inside to be initially deposited on a core, with the stent being subsequently pushed onto the core. Following this, the core is again clamped in and provided with another spun layer. The parameters of the two electrospinning steps may be identical but can also vary, for example to produce a thicker and more porous outer layer. The outer layer is the layer to make contact with the vessel wall and, if applicable, accommodate medical substances.

A stainless steel core is usually employed as mandrel which is later extracted from the construct. Depending on the spinning rate a more or less strong bond is produced between the inner and outer layers across the mesh structure of the stent. A high spin rate is conducive to this bond because the higher solvent content of the deposited fibrils in this case leads to stronger bonding with already spun-coated material.

Further elucidation of the invention is provided through the enclosed figures, where FIG. 1 is a sectional view of an inventive membrane implant with the membrane being of two-layer design;

FIG. 4 is a graphical representation of a membrane implant according to the invention;

FIG. 5 is a photographical representation of a membrane implant according to the invention and FIG. 6 illustrates an enlarged section of a membrane implant as per FIG. 5.

Figure 1:
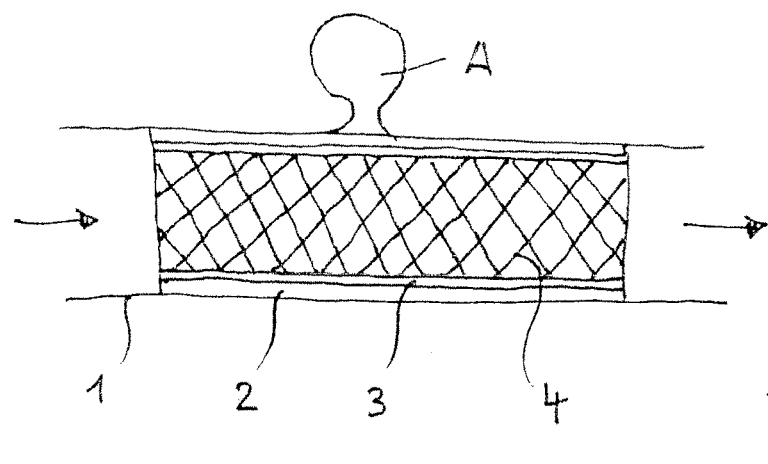

FIG. 1 shows an inventive membrane implant arranged in a blood vessel 1, the membrane of the implant having an outer sponge-like layer 2 in contact with the vessel wall, an inner more or less liquid-tight layer 3 intended to prevent blood passing through the vessel (direction of arrow) from permeating through the membrane as well as the supporting structure or framework of the stent 4 serving to press the membrane against the vessel wall 1. For example, the membrane may serve to isolate an aneurysm A of aciniform shape against the circulating blood flow and in this manner causes the aneurysm to become occluded. However, via its sponge-like outer layer the stent is also capable of accommodating drugs with a view to exerting, for example, an antistenotic effect on the wall of dilated vessels.

Figure 2:
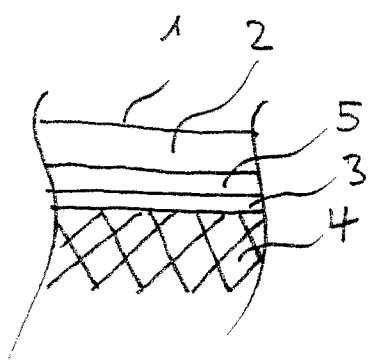
FIG. 2 shows a detail of an inventive membrane implant with the membrane being of three-layer design.

FIG. 2 shows a section of the wall structure of a membrane implant according to the invention with stent 4 on the inside, an adjacent layer 3 designed so as to be substantially liquid-tight, a firm intermediate layer 5, and a sponge-like outer layer 2 intended to be in contact with the vessel wall 1.

It is to be understood that the stent with its framework structure 4 can be integrated into the membrane resulting in the inner smooth layer of the membrane to be arranged on the inside of the stent where it creates a comparatively smooth wall of the implant thus offering only minor resistance against the flow of blood.

Figure 3:
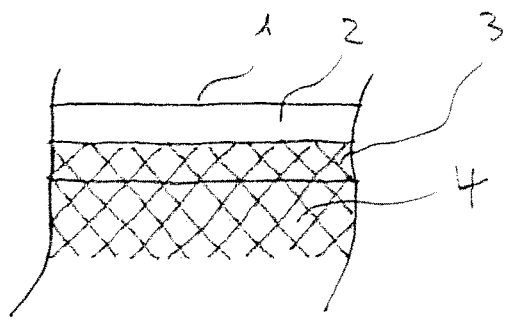
FIG. 3 shows a detail of an inventive membrane implant of a two-layer membrane design, the membrane being arranged on the inside and on the outside of the stent.

FIG. 3 illustrates a section of the wall structure of an inventive membrane implant with stent framework 4, a membrane layer on the inside of the stent framework 4, a second membrane layer on the outside, wherein the layers 2 and 3 are interconnected across the meshes, as well as vessel wall 1.

FIG. 4 shows an inventive membrane implant with stent framework 4 connected to a guidewire 6 via a coupling element 10. In its distal region guidewire 6 is provided with a plastic tube 7 that covers a marker coil 8. A severance point 9 serves to separate the implant from the guidewire, in the present case illustrated here by means of an electrolytic process which is generally known. Alternatively, mechanical severance systems may be provided.

In its central area the stent framework 4 of the membrane implant is provided with a membrane 11 which covers the mesh structure. Marker coils 12 are arranged in the implant's distal region, said coils enable the implant to be accurately placed.

In the illustrated case the stent 4 has been cut from a metal tube, with the stent capable of being guided in compressed form in a catheter and unfolding when it has been released from the catheter. Especially, shape-memory materials are suitably employed, for example nitinol. However, braided stent structures may be used alternatively, in particular those made of nitinol filaments.

FIG. 5 is the photographical representation of a membrane implant according to the invention, with the implant having been released from a catheter tube. Clearly visible are the wire meshes 4 with the membrane covering 11.

FIG. 6 is a photographic enlargement of an inventive membrane implant as shown in FIGS. 4 and 5, illustrating the webs of the framework 4 and the membrane covering which in this case embraces the webs.

The invention claimed is:

1. Membrane implant for the treatment of vascular malformations, said implant being implantable by endovascular methods into the vessel to be treated, wherein the membrane implant comprising an expandable stent (4) and a membrane (2, 3, 5, 11) connected with the stent (4), with said membrane (2, 3, 5, 11) covering the meshes of the stent at least in a central region, characterized in that the membrane (2, 3, 5, 11) is provided in the form of a nonwoven fabric comprising plastic fibrils, wherein the membrane (2, 3, 5, 11) forming a bond with the stent (4) and, at least partially, being of porous design, and wherein the membrane comprises an outer layer facing the wall of the vessel, said outer layer comprising a sponge-like structure that becomes compressed when the stent is expanded in the vessel such that a medical substance in the outer layer is pressed out of the outer layer when the outer layer becomes compressed.

2. Membrane implant according to claim 1, characterized in that the membrane (2, 3, 5, 11) is multi-layered, in particular, of two- or three-layer design.

3. Membrane implant according to claim 1 with a membrane (2, 3, 5, 11) of polycarbonate urethane.

4. Membrane implant according to claim 1 obtained by means of electrospinning of the membrane (2, 3, 5, 11).

5. Membrane implant according to claim 4 obtained by a multi-stage electrospinning process, wherein in a first step an inner membrane (3) is produced on a core, with the stent (4) mounted on the membrane and, subsequently, the outer membrane (2) being arranged and bonded to the inner membrane (3), following which the implant is separated from the core.

6. Membrane implant according to claim 1, characterized in that the membrane (2, 3, 5, 11) embraces the webs of the stent (4) on all sides.

7. Membrane implant according to claim 1, characterized in that the membrane comprises an inner layer (3) that is substantially of liquid-tight and smooth design.

8. Membrane implant according to claim 1, characterized in that the outer layer has a layer thickness of between 10 and 400 µm.

9. Membrane implant according to claim 1, characterized in that the outer layer has pores of a size ranging between 1 and 100 µm in the membrane.

10. Membrane implant according to claim 1, characterized in that the stent (4) is a self-expanding stent made of a shape-memory material.

11. Membrane implant according to claim 10, characterized in that the stent consists of nitinol or a ternary nickel-titanium alloy.

12. Membrane implant according to claim 1, characterized in that the membrane (2, 3, 5, 11) accommodates a medical substance at least in its outer layer (2).

13. Membrane implant according to claim 12, characterized in that the medical substance has an anti-inflammatory or anti-stenotic effect.

14. Membrane implant according to claim 1, characterized in that the membrane (2, 3, 5, 11) accommodates a radiopaque contrast medium.

15. Membrane implant according to claim 1, characterized in that the stent (4) is provided at least on the outside with an adhesion-promoting layer.

16. Membrane implant according to claim 9, wherein the pores are of a size ranging between 10 and 50 µm.

* * * * *